United States Patent [19]
Corey et al.

[11] Patent Number: 5,498,542
[45] Date of Patent: Mar. 12, 1996

[54] ELECTRODE MEDIATORS FOR REGENERATION OF NADH AND NADPH

[75] Inventors: Paul F. Corey, Elkhart; Matthew K. Musho, Granger, both of Ind.

[73] Assignee: Bayer Corporation, Elkart, Ind.

[21] Appl. No.: 314,718

[22] Filed: Sep. 29, 1994

[51] Int. Cl.$^6$ .............. C12M 1/40; G01N 27/00; C07D 279/18; C07D 265/38
[52] U.S. Cl. ............... 435/283.1; 435/817; 435/287.1; 204/403; 544/35; 544/102; 205/777.5
[58] Field of Search .................. 435/4, 288, 177, 435/817; 429/13; 204/153.12, 294, 403; 544/35, 102

[56] References Cited

U.S. PATENT DOCUMENTS 4,490,464  12/1984  Gorton et al. .................. 435/4
4,710,570  12/1987  Thien ........................... 544/31

OTHER PUBLICATIONS

J. Electroanal. Chem. 292 (1990) 115–138.
Persson B., A Comparative Study of Some 3,7 . . . Diaminophen Oxazine. J. Electroanal Chem 292 (1990) 115–138.
Gorton L., Amperometric Glucose Sensors Based on . . . Anal Chim Acta 249 (1991) 43–54.
Gorton L., Electrocatalytic Oxidation of Nad . . . Biosensors & Chemical Sensors ACS Wash DC 1992 Chg. pp. 56–83.

*Primary Examiner*—Ralph J. Gitomer
*Attorney, Agent, or Firm*—Jerome L. Jeffers

[57] ABSTRACT

Disclosed is an electrode suitable for the electrochemical regeneration of the co-enzymes NADH and NADPH. The electrode has imparted on its surface a mediator function which is a 3-methylene-3H-phenothiazine or a 3-methylene-3H-phenoxazine compound.

15 Claims, 1 Drawing Sheet

ELECTRODE MEDIATORS FOR REGENERATION OF NADH AND NADPH

BACKGROUND OF THE INVENTION

Analytical methods that combine the selectivity of enzymes with the sensitivity of amperometric detection are of interest to the diagnostic industry. The reduction of the nicotinamide co-enzymes (NAD and NADP) is particularly important because they are produced in reactions catalyzed by dehydrogenases. Dehydrogenase catalyzed reactions according to the equation:

Substrate–$NAD^+$($NADP^+$) Dehydrogenase$\rightleftarrows$Product+$H^+$+NADH-(NADPH)

play an important role in biological cells and analytical reactions. Several hundred different dehydrogenases are known which selectively catalyze the conversion of different substrates into products. When the substrate, e.g. glucose, is oxidized, the coenzymes $NAD^+$ and/or $NADP^+$ are reduced to NADH and NADPH respectively. These co-enzymes are a necessary element in the reaction due to their ability to act with the dehydrogenase enzyme to form an energy-transferring redox couple. The pyridine linked dehydrogenases transfer reversibly two reducing equivalents from the substrate to the oxidized form of the pyridine nucleotide; one of which appears in the reduced pyridine nucleotide as a hydrogen atom, the other as an electron. The other hydrogen atom removed from the substrate appears as free $H^+$ in the medium.

The co-enzymes $NAD^+$ and $NADP^+$ are expensive chemicals making their regeneration by reoxidation to their original state imperative if they are to be economically used in low cost, disposable, analytical devices. NADH is oxidized directly at different base electrode materials only with high overvoltages on the order of 1 volt. However, a decrease in this overvoltage can be obtained by the immobilization of functionalities on the electrode surface which mediate the electron transfer from NADH to the electrode. Such mediators are typically selected from materials which may be reoxidized electrochemically without excessive overvoltages rendering them useful as an auxiliary system for electrochemical regeneration. Various mediator compounds suitable for this purpose are known. In U.S. Pat. No. 4,490,464 there are mentioned, by way of background, mediators such as phenazine methosulfate (PMS); phenazine ethosulphate (PES); thionine and 1,2-benzoquinone. This patent goes on to describe electrodes which are modified to catalyze the oxidation of NADH, NADPH or analogs thereof by imparting to the electrode surface as mediator a condensed aromatic ring system comprising at least three and preferably four or more condensed aromatic rings with or without heteroatoms. More particularly, this patent describes the electron exchange with the co-enzyme or analog thereof by structural elements comprising one of either alkyl phenazinium ions, phenazinium ions, phenazinones, phenoxazinium ions, phenoxazinones, phenothiazinium ions or phenothiazinones.

In *J. Electroanal. Chem.* 287, 61–80 (1990), there is disclosed 3-β-naphthoyl-toluidine blue O (1),

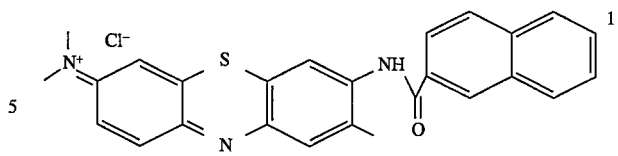

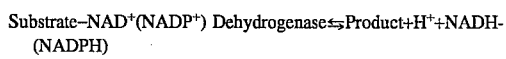

which is perhaps the best known of the phenothiazinium mediators disclosed in the '464 patent.

In *J. Electroanal. Chem.* 292, 115–138 (1990) there are compared a variety of mediators covered by the '464 patent.

The phenoxazinium and phenothiazinium ions disclosed in the '464 patent are positively-charged species such as 1 and are quite different from the compounds useful in the present invention. The phenoxazinones and phenothiazinones disclosed as being useful mediators in the '464 patent are 3H-phenoxazines (A) and 3H phenothiazines (B):

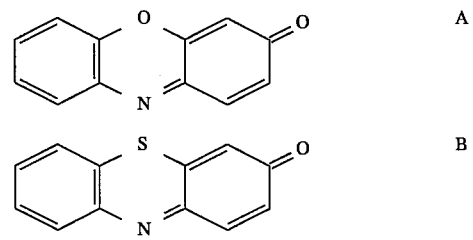

in which the 3-position is derivatized with a carbonyl oxygen group. While they bear a structural resemblance to the mediators of the present invention, in that the oxygen atoms in A and B are replaced by carbon atoms bearing two electron withdrawing substituents, they are chemically quite different and there is no suggestion that replacing the carbonyl oxygen of A or B with a substituted carbon atom would afford effective mediators.

Certain of the compounds whose utility as mediators is disclosed herein are described in U.S. Pat. No. 4,710,570 to be useful as "dye-forming agents in pressure sensitive, thermographic, photothermographic and photographic imaging systems" when in their leuko or reduced form.

SUMMARY OF THE INVENTION

The present invention involves an electrode suitable for the electrochemical regeneration of the co-enzymes dihydronicotinamide adenine dinucleotide (NADH), dihydronicotinamide adenine dinucleotide phosphate (NADPH) or analogs thereof, said electrode having imputed on its surface a mediator function comprising one or more mediator compounds selected from the group consisting of substituted or unsubstituted 3-methylene-3H-phenothiazine and 3-methylene-3H-phenoxazine compounds.

DESCRIPTION OF THE INVENTION

Figure 1:
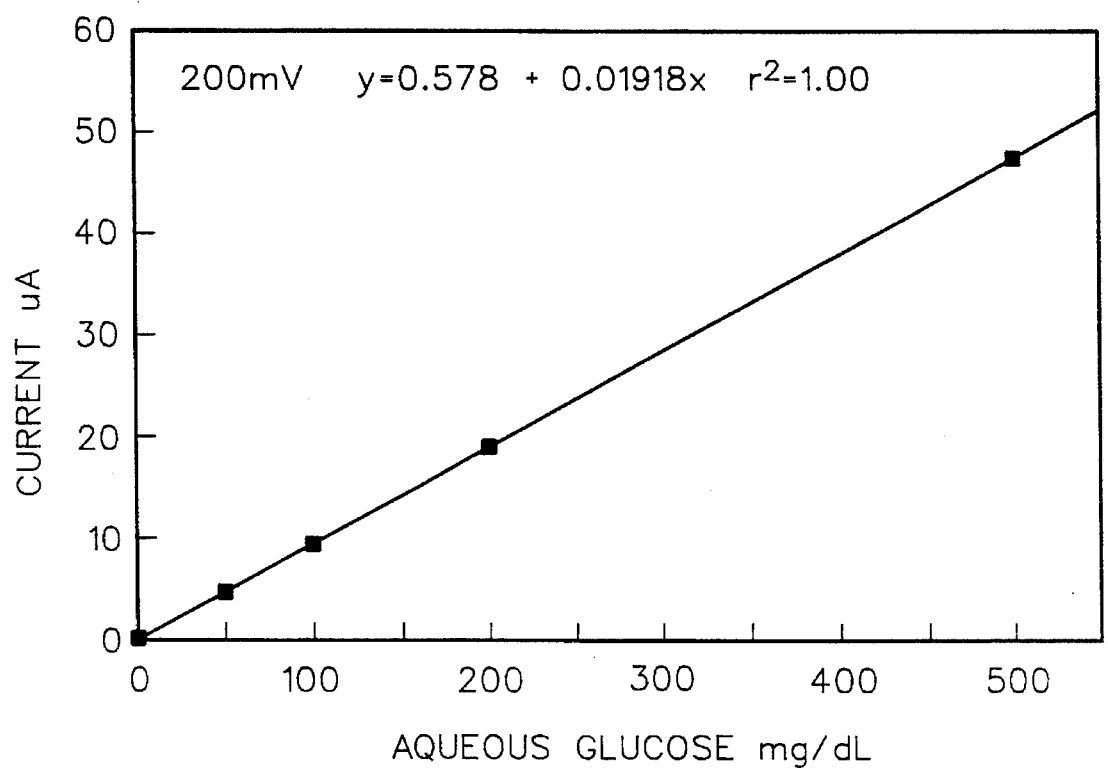
FIG. 1 is a graph in which glucose concentration in mg/dL is plotted against current in μA.

This invention is predicated on the discovery that 3-methylene-3H-phenothiazine and 3-methylene-3H-phenoxazine compounds are useful mediators for the electrochemical regeneration (oxidation) of NADH at a fuel cell electrode. The mediators of the present invention can be represented by general formulae C and D.

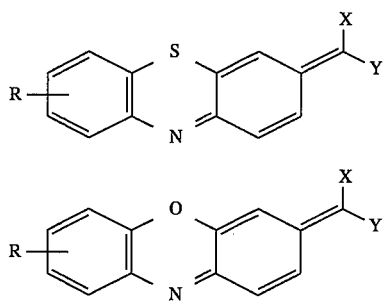

where R is a substituent group attached to the aromatic ring for purposes of modulating the formal potential (E°) or solubility of the mediator, or to provide a functional handle by which the mediator may be linked covalently with other molecules, and X and Y are electron withdrawing groups. More particularly R can represent hydrogen, substituted or unsubstituted aryl (e.g. phenyl, naphthyl, pyridyl), alkoxy (preferably of 1 to 6 carbon atoms), aryloxy, halo (e.g. fluoro, chloro, bromo), nitro, substituted or unsubstituted amino, keto, carboxy or alkoxycarbonyl. The substituents X and Y are selected so as to jointly possess sufficient electron withdrawing capacity to enable the preparation of the compounds of the present invention according to the following Scheme I which is a simplified version of the chemistry of oxidative coupling of carbon acids or active methylene compounds with phenothiazine and phenoxazine.

azine cation (upper right structure). Due to resonance this has a δ+ character on the 3-position and will react with nucleophiles, such as X—CH⁻—Y, to form an initial adduct which is oxidized (losing 2H) to give mediators C. The chemistry for the preparation of phenoxazine compounds D is analogous. The Thien patent (U.S. Pat. No. 4,710,570) describes this as an oxidative coupling. For this reaction to work the protons of X—CH$_2$—Y must be acidic enough to form X—CH⁻—Y under the reaction conditions which typically involve the use of potassium acetate in methanol. If X—CH$_2$—Y is not sufficiently acidic there results an unstable dimer characterized as a "phenothiazine green cation" by Diudea [Tet. Letters 23, 1367–1370 (1982)] and isolated as its perchlorate salt by Tsujino [Nippon Kagaku Zasshi 91 (11), 1080-5 (1970); Chem. Abs. 74, 125598k (1971)]. It is formed in high yield under the conditions of Scheme I if the X—CH$_2$—Y is left out or if it isn't acidic enough. One skilled in this art can readily determine if X and Y together possess insufficient electron withdrawing character by running the coupling reaction of Scheme I. If the resultant is phenothiazinium green, then X and Y together do not possess the requisite electron withdrawing capability. Suitable X and Y moieties include, but are not limited to: cyano, aliphatic and aromatic keto, aliphatic and aromatic ester, substituted or unsubstituted amido, trifluoromethylsulfonyl, trifluoromethylketo, nitro, lower alkyl sulfonyl, trifluoromethylsulfinyl, arylsulfonyl, lower alkylketo, lower alkylsulfinyl and arylsulfinyl. Other suitable electron withdrawing moieties include polyhaloalkyl, perfluorophenyl,

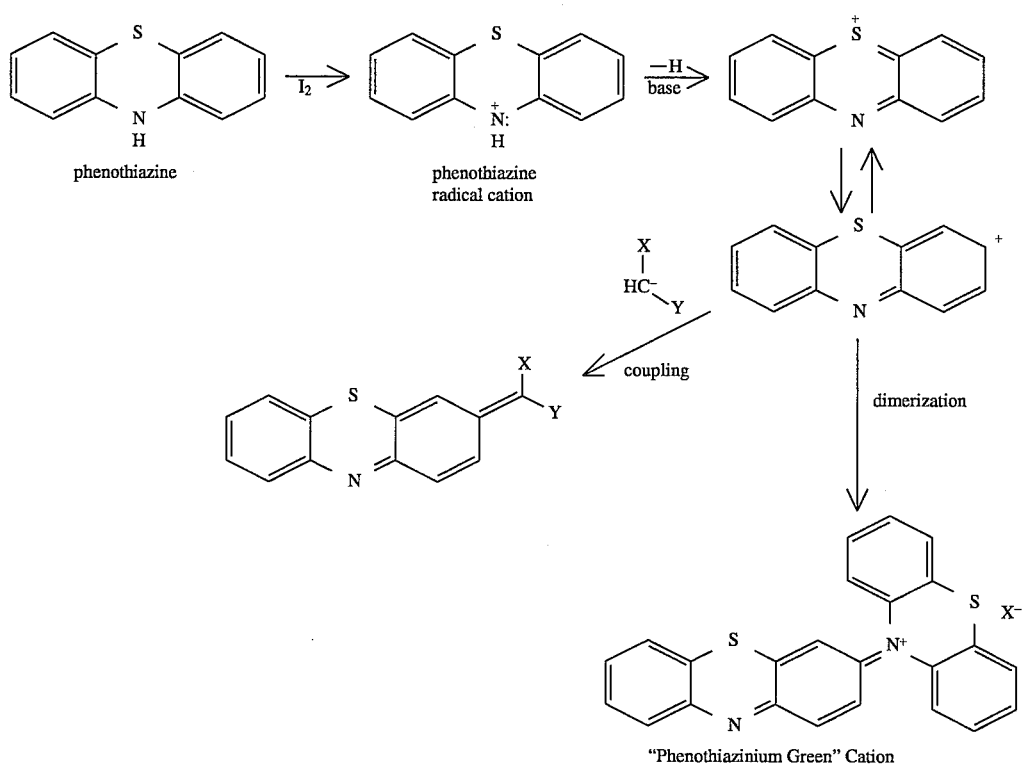

Scheme I

If the combined electron withdrawing character of X and Y is not great enough, the compounds cannot be prepared according to this synthesis technique. Referring to Scheme I, phenothiazine reacts with an oxidant/electron acceptor, such as iodine (I$_2$), to form a radical cation which under alkaline conditions loses a proton and gives rise to phenothi- 2-benzoxazolyl, 2-benzthiazoyl and 5-Cl-tetrazolyl. Structures in which X and Y make up a 1,3-diketone are also suitable. For example X and Y can make up a cyclic 1,3-diketone such as indane-1,3-dione or 5,5-dimethyl-1,3-cyclohexanedione (dimedone), cyclic esters such as Meldrum's acid or a cyclic amide such as N,N-dialkylbarbituric acid. While some routine experimentation may be required to determine whether a given set of X and Y substituents possess the requisite electron withdrawing capability, there are disclosed in Bordwell's article [Acc. Chem. Res. 21, 456–463 (1988) and references cited therein] the equilibrium acidities in dimethylsulfoxide (DMSO) for a wide variety of carbon acids, including many X—$CH_2$—Y compounds. The greater the electron withdrawing character of X and Y, the lower the pKa. In general, compounds X—$CH_2$—Y with equilibrium acidities (in DMSO @ 25° C.)≦13.1 will react well; those having a pKa between about 13.1 and about 15.8 will react to a lesser degree and those with a pKa≧15.8 will not react at all.

Compounds C and D can be represented by a single formula E in which the symbol Z is used to represent oxygen and sulfur.

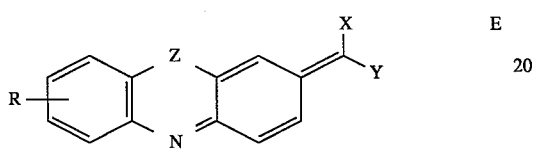

It will be evident that the rings of these compounds as well as aliphatic or aromatic groups appended thereto can bear a variety of substituent groups which do not adversely affect their electron transport properties without departing from the scope of the present invention. Such substituent groups are limited only by the ability of one of ordinary skill in this art to prepare stable compounds which have the electrochemical properties necessary for the requisite electron transport.

Nicotinamide adenine dinucleotide (oxidized form, $NAD^+$; reduced form, NADH) is the cofactor providing chemical redox function for many dehydrogenase enzymes. This cofactor is reduced during the course of the enzymatic reaction as the substrate molecule is oxidized. Amperometric biosensors seeking to use these enzymes as a means to measure substrate concentration correlate this concentration with the current generated as the cofactor is electrochemically re-oxidized. The NADH can be electrochemically re-oxidized on graphite, pyrolytic carbon, glassy carbon, platinum or gold electrodes without a mediator, but this reaction occurs with several difficulties including a large overpotential and electrode fouling.

The present invention describes the first use of 3-methylene-3H-phenothiazines (C) and 3-methylene-3H-phenoxazines (D) in the electrochemical regeneration of NADH and NADPH coenzymes or their derivatives and accordingly, encompasses a wide variety of phenothiazine and phenoxazine derivatives. The present mediators can also be used for the electrochemical regeneration of NADH and NADPH derivatives. Derivatives of NADH and NADPH such as in the case where the coenzyme is attached to a polymer are described by Dolabdjian, et al in *Enzyme Engineering* Vol. 4, G. B. Brown and G. Manecke, eds., Plenum Press, New York, 1978, Pp. 399–400 or covalently attached to the dehydrogenase enzyme as described by M. Persson, et al in *Biotechnology* 9, Pp. 280–284 (1991) or synthetic analogs bearing other substituents so long as they function as the cofactor for the dehydrogenase enzyme. These references are incorporated herein by reference.

The mediator compounds of this invention may be depicted by the general structures C and D. There have been evaluated 10 different analogs as mediators on graphite rod electrodes; their structures are as follows:

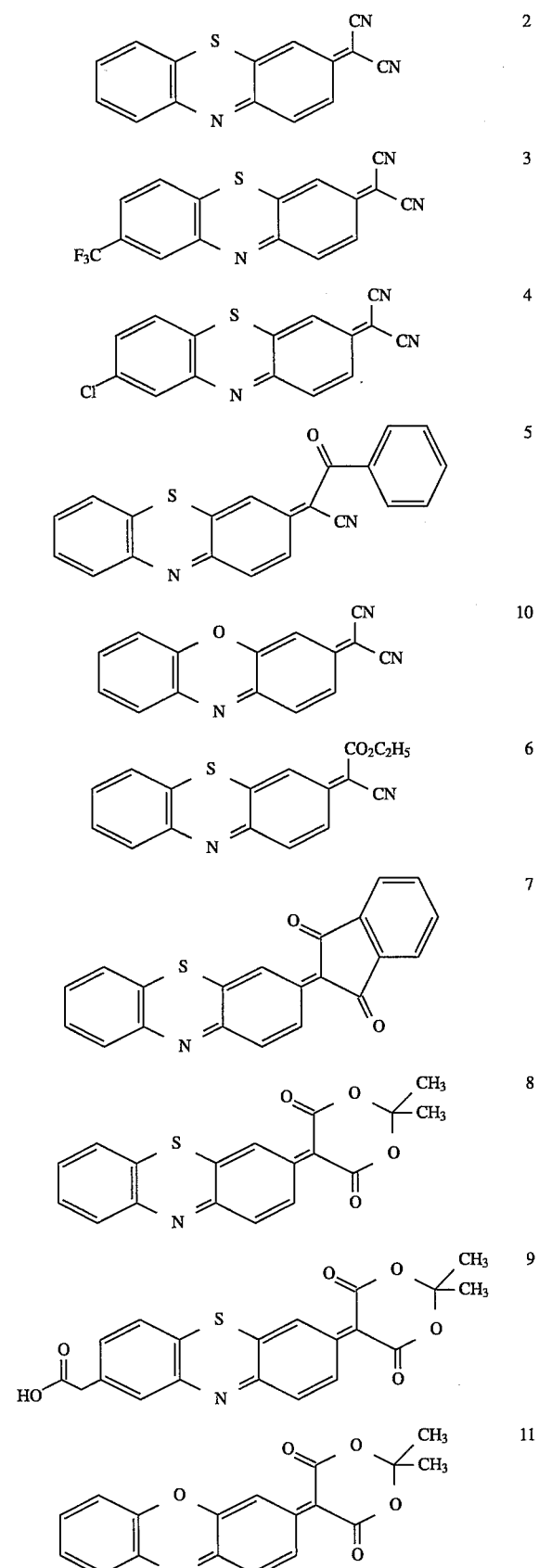

These compounds were prepared according to the following examples:

EXAMPLE I

Synthesis of Mediators

The synthesis of compounds 2, 3, 5, 6, 10 and 11 is disclosed in U.S. Pat. No. 4,710,570 whose disclosure is incorporated herein by reference. Compounds 4, 7, 8 and 9 were prepared as follows:

3-Dicyanomethylene-8-chloro-3H-phenothiazine (4):

A solution of 2-chlorophenothiazine (1.0 g; 4.26 mmol) and potassium acetate (KOAc) (2.5 g) in boiling methanol (MeOH) (70 mL) was allowed to cool to 40° C. then treated with malononitrile (0.42 g; 1.5 eq). This solution was treated at once with a solution of $I_2$ (2.16 g) in MeOH (25 mL) and allowed to stir at ambient temperature for 3.5 h. The dark green solid that separated was collected by filtration, washed with MeOH and dried in vacuo to give 4 (0.33 g, 26%). MS (70 eV) m/e (rel. intensity) 295 (100), 260 (26).

3-(1,3-dioxo-indanylidene-(2'))-3H-phenothiazine (7):

A solution of phenothiazine (2.0 g; 10 mmol) and KOAc (4.0 g) in boiling MeOH (60 mL) was allowed to cool to 53° C. then treated with 1,3-indandione (2.2 g; 1.5 eq). This solution was allowed to cool to 30° C., treated with a solution of $I_2$ (3.0 g) in MeOH (50 mL) and allowed to stir at ambient temperature for 18.5 h. The dark solid that separated was collected by filtration, washed with MeOH and dried in vacuo to give 7 (0.13 g, 3.8%). MS (70 eV) m/e (rel. intensity) 341 (100), 284 (36).

3-(2,2-dimethyl-4,6-dioxo-1,3-dioxanylidene-(5'))-3H-phenothiazine (8):

A solution of phenothiazine (1.02 g; 5.13 mmol) and KOAc (3.0 g) in boiling MeOH (40 mL) was allowed to cool to 24° C. then treated with 2,2-dimethyl-1,3-dioxane-4,6-dione (2.0 g; 2.7 eq). This solution was allowed to cool to 21° C., treated with a solution of 12 (2.6 g) in MeOH (50 mL) and allowed to stir at ambient temperature for 3 h. The dark solid that separated was collected by filtration, washed with MeOH and dried in vacuo to give 8 (0.62 g, 35%). $^1$H NMR (300 MHz) (CDCl$_3$) δ 8.85–8.95 (m, 2H), 7.95–8.05 (m, 1H), 7.67 (d, J=9.96 Hz, 1H), 7.50–7.60 (m, 3H), 1.77 (s, 6H); MS (70 eV) m/e (rel. intensity) 339 (12), 281 (65), 253 (19), 237 (56), 209 (100).

3-(2,2-dimethyl-4,6-dioxo-1,3-dioxaylidene-(5'))-3H-phenothiazine-8-acetic acid (9):

A solution of phenothiazine-2-acetic acid [prepared according to the method of Massie et al. in *J. Org. Chem.* 21, 1006 (1956)] (0.33 g; 1.28 mmol) and lithium acetate dihydrate (0.66 g, 5 eq) in MeOH (7 mL) at ambient temperature, was treated with 2,2-dimethyl-1,3-dioxane-4,6-dione (0.5 g; 2.7 eq) and additional MeOH (1.5 mL). This solution was treated with a solution of $I_2$ (0.65 g, 2 eq) in MeOH (5 mL), stirred for 2.3 h. then chilled in an ice bath. The dark solid that separated was collected, washed with ice-cold MeOH and dried in vacuo to give 9 (60.8 mg, 12%). $^1$H NMR (300 MHz) (CDCl$_3$) δ 8.87 (d of d, $J_1$+2.0 Hz and $J_2$=9.96 Hz, 1H), 8.83 (d, J=2.0 Hz, 1H), 7.91 (d, J=1.3 Hz, 1H), 7.59 (d, J=9.96 Hz, 1H), 7.45–7.55 (M, 2H), 3.80 (s, 2H), 1.77 (s, 6H).

EXAMPLE II

Evaluation as Mediators

Graphite rod electrodes (3 mm in diameter from Johnson Matthey Electronics, Ward Hill, Mass.) were prepared by polishing the electrode's surface using first a fine grit sandpaper and then a suspension of ≦1 micron alumina particles. A 1 mM methanolic solution of the mediator was prepared and the electrode was soaked in this solution for 2 minutes. The electrodes were then rinsed with water and soaked for a short time in 0.25M phosphate buffer (pH=7). At this point a current -vs- voltage profile was run to determine the cathodic and anodic peak positions -vs- Ag/AgCl reference electrodes. Currents were then measured in pH=7 solutions containing NADH in concentrations from 20 to 200 μM, using a potential that was typically 100 mv more positive than the oxidation peak, and the slope of the line obtained from a least squares fit of the current -vs- NADH concentration data gave the relative sensitivity of each mediator in μA/μM NADH. These slopes are set out in Table I (Column 4) together with the structure of mediators tested (Column 1) and their oxidation potentials ($E°_{ox}$) (Column 2). The greater the slope the more sensitive the mediator.

TABLE I

| Compound | NADH $E°_{ox}$ | Titration on GRE Potential | Slope | Glucose $E°_{ox}$ | Titration on Sensor Potential | Slope |
|---|---|---|---|---|---|---|
| 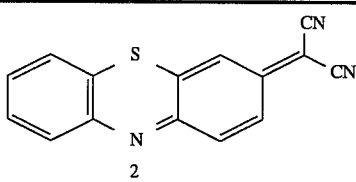 2 | −68 mv | | 0.0020 | | | |
| 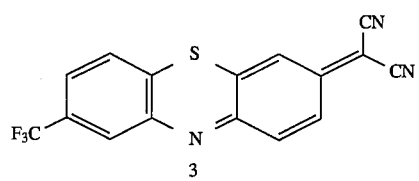 3 | −17 mv | | 0.0032 | | | |

TABLE I-continued

| Compound | NADH $E^\circ_{ox}$ | Titration on GRE Potential | Slope | Glucose $E^\circ_{ox}$ | Titration on Sensor Potential | Slope |
|---|---|---|---|---|---|---|
| 4 | +2 mv | — | | | | |
| 5 | +77 mv | | 0.0037 | | | |
| 6 | −74 mv | | 0.0039 | | | |
| 7 | −41 mv | | 0.0026 | | | |
| 8 | +55 mv | | 0.0074 | | | |
| 9 | | | | +5 mv | 200 mv | 0.01918 |
| 10 | −126 mv | | 0.0025 | | | |

TABLE I-continued

| Compound | NADH $E°_{ox}$ | Titration on GRE Potential | Slope | Glucose $E°_{ox}$ | Titration on Sensor Potential | Slope |
|---|---|---|---|---|---|---|
| 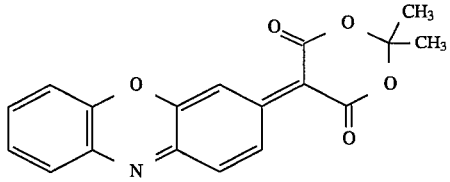 11 | | −2 mv | 0.0061 | | | |
| 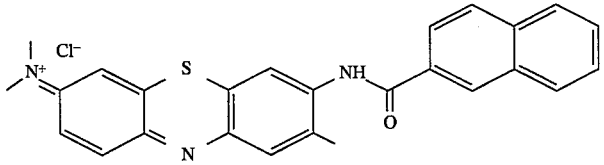 1 | | +60 mv | 0.010 | | | |

EXAMPLE III

Evaluation of Mediators on Printed Electrodes

Experiments involving printed electrodes comprising a printed sensor card with a graphite/carbon working electrode and a silver/silver chloride reference electrode were carried out. The ink used for the graphite/carbon electrode was No. 423SS (from Acheson Colloids Co., Port Huron, Mich.) and No. 427SS silver ink (same vendor) blended with 15–25% AgCl for the silver/silver chloride reference electrode. Electrode surface area was 0.03 cm².

A typical glucose biosensor may be fabricated as follows: A solution of 4 mM 9 in 100 mM pH=7.0 PIPES buffer containing 27 mM KCl was prepared and diluted with an equal volume of a solution composed of 1.96 g 0.5% FC-170C surfactant (3M Company; St. Paul, Minn.), 0.142 g NAD, 0.626 g Glucose Dehydrogenase (GDH) (Toyobo Co., Ltd.; Osaka, Japan), 1.44 g 0.5M PIPES buffer pH=7.0 containing 147 mM KCl, and 5.83 mL DI $H_2O$. The mixture, 3.0μ, was applied to the sensor area and allowed to dry at room temperature for about 20 minutes. The electrode was assembled in a format having a small capillary gap, treated with a solution of aqueous glucose and the current measured at a potential of 200 mv. This was done for samples containing glucose concentrations of 0, 50, 100, 200 and 500 mg/dL and the slope of the line obtained from a least squares fit of the current vs. glucose concentration data gave a glucose response of 0.01918 μA/mg dL$^{-1}$ glucose.

FIG. 1 shows the plot of current vs. glucose concentration for compound 9 at 200 mv potential. This represents a dose response plot of complete sensors measuring different concentrations of glucose. From FIG. 1 it can be determined that sensors constructed as described herein respond linearly over the physiologically relevant glucose range. The high sensitivity to glucose (19 μA per mg/dL) and low intercept while operating at low applied potential (200 mv) is important for constructing clinically useful instruments. With appropriate calibration it is possible to correlate measured current from the sensor with glucose concentration in an unknown solution.

What is claimed is:

1. An electrode for the electrochemical regeneration of the coenzymes dihydronicotinamide adenine dinucleotide (NADH), dihydronicotinamide adenine dinucleotide phosphate (NADPH) or analogs thereof wherein there has been imparted to the electrode surface a mediator comprising one or more mediator compounds selected from the group consisting of substituted or unsubstituted 3-methylene-3H-phenothiazine and 3-methylene-3H-phenoxazine compounds represented by the formula:

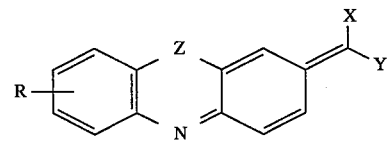

wherein Z is oxygen or sulfur, R is hydrogen, substituted or unsubstituted aryl, alkoxy, aryloxy, halo, nitro, substituted or unsubstituted amino, keto, carboxy or alkoxycarbonyl and X and Y are electron withdrawing groups.

2. The electrode of claim 1 wherein the aryl group is phenyl, naphthyl or pyridyl; the halo group is fluoro, chloro or bromo and the alkoxy group contains 1 to 6 carbon atoms.

3. The electrode of claim 1 wherein X and Y are independently cyano, aliphatic or aromatic keto, aliphatic or aromatic ester, substituted or unsubstituted amido, trifluoromethylsulfonyl, trifluoromethylketo, nitro, lower alkylsulfonyl, trifluoromethylsulfinyl, arylsulfonyl, lower alkylketo, lower alkylsulfinyl, arylsulfinyl, polyhaloalkyl, perfluorophenyl, 2-benzoxazolyl, 2-benzthiazolyl or 5-Cl-tetrazolyl.

4. The electrode of claim 1 wherein X and Y together make up a cyclic 1,3 ketone; a cyclic ester or a cyclic amide.

5. The electrode of claim 1 wherein the mediator is represented by the formula:

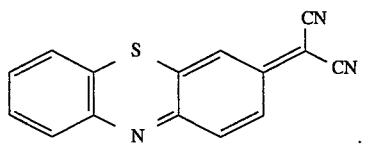

6. The electrode of claim 1 wherein the mediator is represented by the formula:

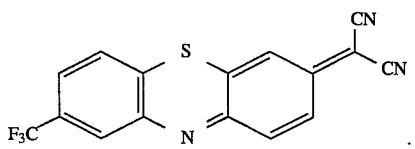

7. The electrode of claim 1 wherein the mediator is represented by the formula:

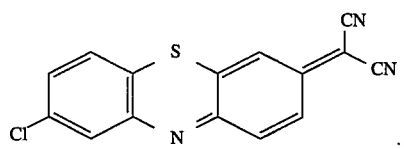

8. The electrode of claim 1 wherein the mediator is represented by the formula:

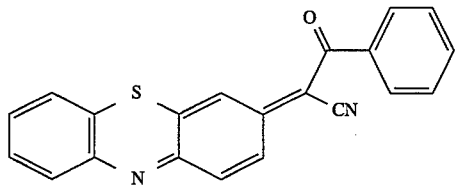

9. The electrode of claim 1 wherein the mediator is represented by the formula:

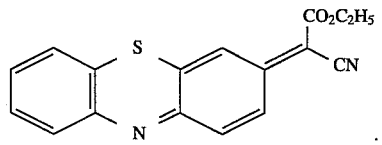

10. The electrode of claim 1 wherein the mediator is represented by the formula:

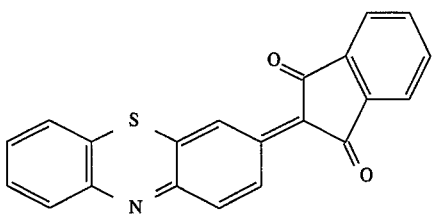

11. The electrode of claim 1 wherein the mediator is represented by the formula:

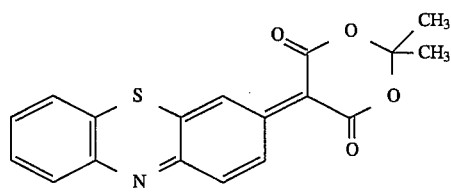

12. The electrode of claim 1 wherein the mediator is represented by the formula:

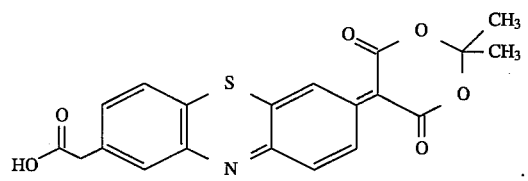

13. The electrode of claim 1 wherein the mediator is represented by the formula:

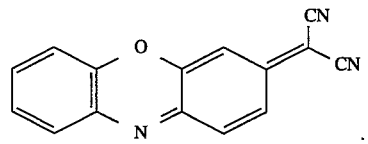

14. The electrode of claim 1 wherein the mediator is represented by the formula:

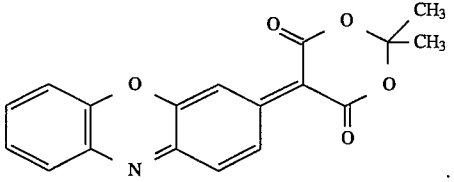

15. The electrode of claim 1 comprising graphite, pyrolytic carbon, glassy carbon, platinum or gold.

* * * * *